(12) United States Patent
Del Antonio et al.

(10) Patent No.: US 11,558,082 B2
(45) Date of Patent: Jan. 17, 2023

(54) EMC SHIELDING FOR CONTACTLESS DATA TRANSMISSION

(71) Applicant: Siemens Healthcare GmbH, Erlangen (DE)

(72) Inventors: Marco Del Antonio, Coswig (DE); Ludwig Welker, Eggolsheim (DE); Sebastian Hierl, Leipzig (DE); Philipp Quednau, Erlangen (DE); Roman Gloeckler, Lauf a. d. Pegnitz (DE); Volker Model, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/540,598

(22) Filed: Dec. 2, 2021

(65) Prior Publication Data

US 2022/0182101 A1 Jun. 9, 2022

(30) Foreign Application Priority Data

Dec. 9, 2020 (DE) ...................... 10 2020 215 568.2

(51) Int. Cl.
*H04B 5/00* (2006.01)
*H04B 1/00* (2006.01)
(Continued)

(52) U.S. Cl.
CPC ......... *H04B 5/0031* (2013.01); *H05K 9/0018* (2013.01); *A61B 6/56* (2013.01)

(58) Field of Classification Search
None
See application file for complete search history.

(56) References Cited

U.S. PATENT DOCUMENTS

| 5,530,422 A | 6/1996 | Harrison |
| 5,577,026 A | 11/1996 | Gordon et al. |

(Continued)

FOREIGN PATENT DOCUMENTS

| CN | 101076243 A | 11/2007 |
| CN | 106793985 A | 5/2017 |

(Continued)

OTHER PUBLICATIONS

German Office Action and English translation thereof dated Oct. 14, 2021.

(Continued)

*Primary Examiner* — Tuan A Tran
(74) *Attorney, Agent, or Firm* — Harness, Dickey & Pierce, P.L.C.

(57) ABSTRACT

A device includes a first and a second part, relatively rotatable, and data transmission structures for contactless transmission of data. The data transmission structures include a transmit and/or receive facility a coupling facility on the two parts. The transmit and/or receive facility extends over a small angle and the coupling facility extends over a complete circle. Data is transmitted between the facilities at a transmission frequency. The two parts include walls encompassing a tunnel interior space extending completely around the axis of rotation. The data transmission structures are arranged in the tunnel interior space. The walls are electrically conductive structures reflecting electromagnetic alternating fields in the transmission frequency range. An absorber structure is arranged at least on a part of the walls toward the tunnel interior space and the absorber structure absorbs electromagnetic alternating fields in the range of the transmission frequency.

19 Claims, 7 Drawing Sheets

(51) Int. Cl.
    *A61B 6/00*           (2006.01)
    *A61B 6/03*           (2006.01)
    *H05K 9/00*          (2006.01)
    *H05G 1/08*           (2006.01)
    *H05G 1/10*           (2006.01)

(56) References Cited

U.S. PATENT DOCUMENTS

| | | | | |
|---|---|---|---|---|
| 7,043,114 | B2 * | 5/2006 | Popescu | G02B 6/4202 |
| | | | | 385/27 |
| 7,240,251 | B2 * | 7/2007 | Popescu | H04L 1/24 |
| | | | | 714/704 |
| 7,421,058 | B2 * | 9/2008 | Popescu | A61B 6/035 |
| | | | | 333/24 R |
| 7,423,257 | B2 * | 9/2008 | Popescu | A61B 6/035 |
| | | | | 250/227.14 |
| 7,466,791 | B2 * | 12/2008 | Krumme | A61B 6/56 |
| | | | | 378/15 |
| 7,466,794 | B2 * | 12/2008 | Krumme | H04B 10/801 |
| | | | | 378/19 |
| 7,755,055 | B2 * | 7/2010 | Schilling | A61B 6/56 |
| | | | | 250/370.09 |
| 7,860,126 | B2 * | 12/2010 | Popescu | A61B 6/56 |
| | | | | 370/473 |
| 7,899,150 | B2 * | 3/2011 | Beyerlein | A61B 6/56 |
| | | | | 378/101 |
| 8,126,298 | B2 * | 2/2012 | Stark | G08C 17/06 |
| | | | | 385/26 |
| 8,129,865 | B2 * | 3/2012 | Krumme | H02P 9/10 |
| | | | | 307/104 |
| 8,447,010 | B2 * | 5/2013 | Reichel | A61B 6/56 |
| | | | | 378/19 |
| 8,594,480 | B2 * | 11/2013 | Krumme | A61B 6/56 |
| | | | | 378/19 |
| 9,748,802 | B2 * | 8/2017 | Krumme | H01F 38/14 |
| 9,757,089 | B2 * | 9/2017 | Reichel | A61B 6/56 |
| 9,764,161 | B2 * | 9/2017 | Mazin | A61N 5/1081 |
| 9,813,004 | B2 * | 11/2017 | Shrestha | H02K 3/28 |
| 9,820,700 | B2 * | 11/2017 | Mazin | A61N 5/1067 |
| 9,859,994 | B2 * | 1/2018 | Steffens | H04B 17/27 |
| 2005/0013535 | A1 * | 1/2005 | Popescu | A61B 6/56 |
| | | | | 398/116 |
| 2009/0220042 | A1 * | 9/2009 | Festag | A61B 6/56 |
| | | | | 378/15 |
| 2011/0069819 | A1 * | 3/2011 | Urban | A61B 6/56 |
| | | | | 378/197 |
| 2013/0214181 | A1 | 8/2013 | Delpech et al. | |
| 2013/0259202 | A1 | 10/2013 | Sloutsky et al. | |
| 2015/0036791 | A1 | 2/2015 | Reichel | |
| 2017/0181723 | A1 * | 6/2017 | Abraham | A61B 6/56 |
| 2017/0215833 | A1 | 8/2017 | Krumme | |
| 2019/0015060 | A1 * | 1/2019 | Weiss | A61N 5/1039 |

FOREIGN PATENT DOCUMENTS

| | | | | |
|---|---|---|---|---|
| DE | 19533820 A1 | | 3/1996 | |
| DE | 102013215045 A1 | | 2/2015 | |
| DE | 102016223007 A1 | | 12/2017 | |
| WO | WO 2005/040777 | * | 5/2005 | A61B 6/00 |
| WO | WO 2010/062464 | * | 6/2010 | A61B 6/03 |

OTHER PUBLICATIONS

German Decision to Grant and English translation thereof dated Feb. 2, 2022.

* cited by examiner f (GHz)

EMC SHIELDING FOR CONTACTLESS DATA TRANSMISSION

PRIORITY STATEMENT

The present application hereby claims priority under 35 U.S.C. § 119 to German patent application number DE 10 2020 215 568.2 filed Dec. 9, 2020, the entire contents of each of which are hereby incorporated herein by reference.

FIELD

Example embodiments of the invention generally relate to a device,
  wherein the device has a first and second part,
  wherein one of these two parts is a part that is able to rotate relative to the other part about an axis of rotation,
  wherein the device has data transmission structures for the contactless transmission of data,
  wherein the data transmission structures comprise a transmit and/or receive facility, which is arranged on the first part, and a coupling facility which is arranged on the second part,
  wherein, viewed in the circumferential direction about the axis of rotation, the transmit and/or receive facility extends over a small angle and the coupling facility extends over a complete circle,
  wherein data is transmitted between the transmit and/or receive facility and the coupling facility at a transmission frequency.

BACKGROUND

A device is known for example from DE 10 2016 223 007 A1.

Data can be transmitted between stationary and rotating system components of a device as required in a contact-based manner (for example by way of slip rings) or in a contactless manner.

In the case of a contactless data transmission, the operating principle is based on electromagnetic alternating fields that propagate in the room. In some cases of contactless data transmission, it is merely necessary to arrange a transmit and/or receive facility in each case on the two system components between which data is to be transmitted and to transmit the data via antenna or the like. However, due to the propagation in the room, the electromagnetic alternating fields can also couple into other electrical conductors and interfere with the information transfer that is taking place (keyword EMC=electromagnetic compatibility). This can affect the functionality of other components and systems of the device or other electromagnetic facilities that are arranged in the environment of the device.

In some cases, the electromagnetic interferences can be accepted. In other cases, they cannot be tolerated. In such cases, data is transmitted by way of data transmission structures, such as are described above. In this case, a further transmit and/or receive facility is arranged on the second part. Data can be transmitted between the coupling facility and the further transmit and/or receive facility as required in a contactless or contact-based manner.

In the prior art, a local cover is provided in the region of the transmit and/or receive facility that is arranged on the first part. This cover is often located at a specific distance (a few millimeters) from the second part. Data transmissions in the MHz range can be shielded via covers of this type.

SUMMARY

In recent times, data is transmitted ever more frequently at transmission frequencies that lie in the GHz range, for example in the range between 3 GHz and 30 GHz. The inventors have discovered that the covers used in the prior art are not suitable for transmissions at such high frequencies.

At least one embodiment of the present invention creates possibilities by which reliable shielding is possible even in the case of transmission frequencies in the GHz range.

Advantageous embodiments of the device in accordance with the invention are the subject matter of the claim.

In accordance with at least one embodiment of the invention, a device is configured by virtue of the fact,
  that the first and the second part have walls that jointly completely encompass a tunnel interior space that extends completely around the axis of rotation,
  that the data transmission structures are arranged in the tunnel interior space or protrude into the tunnel interior space,
  that the walls are formed as electrically conductive structures with the result that they reflect electromagnetic alternating fields in the range of the transmission frequency, and
  that an absorber structure is arranged at least on a part of the walls toward the tunnel interior space and the absorber structure absorbs electromagnetic alternating fields in the range of the transmission frequency.

At least one embodiment is directed to a device, comprising:
  a first part and second part, one of the first part and the second part being a part rotatable relative to another one of the first part and the second part, about an axis of rotation;
  data transmission structures for contactless transmission of data, the data transmission structures including at least one of a transmit and receive facility, arranged on the first part, and a coupling facility arranged on the second part,
  wherein, when viewed in a circumferential direction about the axis of rotation, the at least one of transmit and receive facility extends over a small angle and the coupling facility extends over a complete circle,
  wherein data is transmitted between the at least one of transmit and receive facility and the coupling facility at a transmission frequency,
  the first part and the second part including walls jointly completely encompassing a tunnel interior space extending completely around the axis of rotation,
  the data transmission structures being arranged in the tunnel interior space or protruding into the tunnel interior space,
  the walls being formed as electrically conductive structures configured to reflect electromagnetic alternating fields in a range of the transmission frequency; and
  an absorber structure, arranged at least on a part of the walls toward the tunnel interior space, to absorb electromagnetic alternating fields in the range of the transmission frequency.

BRIEF DESCRIPTION OF THE DRAWINGS

The above-described characteristics, features and advantages of this invention and the manner in which these are achieved are more clearly and more precisely understandable in conjunction with the following description of the example embodiments that are further explained in connection with the drawings. The drawings illustrate in a schematic view.

DETAILED DESCRIPTION OF THE EXAMPLE EMBODIMENTS

Figure 1:
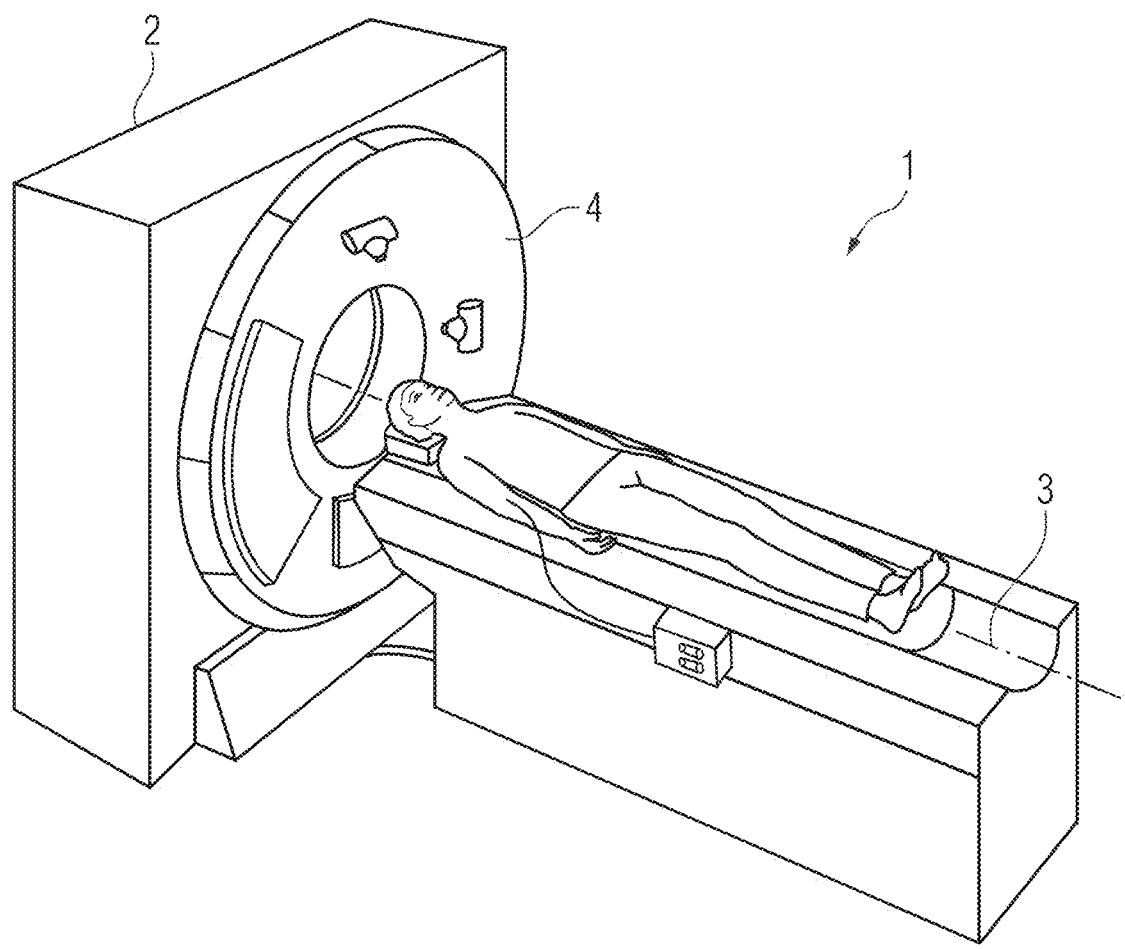
FIG. 1 a computed tomography unit,
FIG. 2 a second part from the front,
FIG. 3 the second part shown in FIG. 2 viewed from the side,
FIG. 4 a data transmission path,
FIG. 5 a part region of the second part shown in FIG. 2,
FIG. 6 a part region of the second part shown in FIG. 2, including a wall,
FIG. 7 an enlarged view of a section shown in FIG. 6,
FIG. 8 the second part shown in FIG. 2 viewed from the side, including the wall,
FIG. 9 a detail from FIG. 7,
FIG. 10 a cut-out and a transceiver,
FIG. 11 the elements shown in FIG. 10 without the wall in the region of the transceiver and
FIG. 12 a possible embodiment of a flexible material.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In accordance with at least one embodiment of the invention, a device is configured by virtue of the fact,
  that the first and the second part have walls that jointly completely encompass a tunnel interior space that extends completely around the axis of rotation,
  that the data transmission structures are arranged in the tunnel interior space or protrude into the tunnel interior space,
  that the walls are formed as electrically conductive structures with the result that they reflect electromagnetic alternating fields in the range of the transmission frequency, and
  that an absorber structure is arranged at least on a part of the walls toward the tunnel interior space and the absorber structure absorbs electromagnetic alternating fields in the range of the transmission frequency.

It is preferred that the walls in the transition regions from the first part to the second part are formed as elastic structures having two ends, wherein the one end of the elastic structures is fastened to a respective retaining structure that is arranged on the first or on the second part and the other end of the elastic structures is pressed onto the second or the first part. As a consequence, gaps and similar interruptions of the tunnel are avoided. It is therefore not possible for the electromagnetic alternating fields to escape from the tunnel interior space. The elastic structures can be designed for example as brush hairs.

It is preferred that the retaining structures are spaced apart from one another with regard to the axis of rotation in an axial and/or radial manner and a carrier plate that bridges the retaining structures is inserted into the retaining structures. This embodiment is particularly simple to realize as far as the construction is concerned.

It is preferred that the retaining structures have receiving facilities for receiving the carrier plate and that arranged in the receiving facilities are lamellae via which the receiving facilities are electromagnetically sealed with respect to the carrier plate in the range of the transmission frequency and the carrier plate is mechanically fixed in the receiving facilities. This embodiment combines a relatively simple construction with reliable shielding.

It is preferred that the absorber structure is arranged on the carrier plate. As a consequence, in particular the absorber structure can be arranged in a simple manner toward the tunnel interior space.

It is preferred that the retaining structures are arranged on the first part (in other words not on the second part). This embodiment renders possible in particular a simple electromagnetic "seal" with respect to the transmit and/or receive facility.

It is preferred that the absorber structure is designed as a foam. As a consequence, the absorber structure is particularly efficient with respect to its electromagnetic properties.

It is preferred that the wall that is arranged on the first part is formed from a flexible material at least in its region that is adjoining the transmit and/or receive facility. As a consequence, it is possible to achieve a particularly good and reliable electromagnetic "seal" with respect to the transmit and/or receive facility. The flexible material can be for example a conductive material or a conductive fabric. It is of importance in this case that the flexible material—at least preferably—does not have any inherent stability. As a consequence, although the flexible material lies in a sealing manner against the transmit and/or receive facility, the flexible material does not exert any force on the transmit and/or receive facility. In particular, adjustments to the transmit and/or receive facility are consequently not impaired by the flexible material.

It is possible for the wall that is arranged on the first part to likewise be formed from a flexible material of this type outside the region that is adjoining the transmit and/or receive facility. However, as an alternative, it is also possible that the wall that is arranged on the first part is formed from an inherently stable material, in certain circumstances even from a rigid material, outside the region that is adjoining the transmit and/or receive facility. A material that assumes and retains a specific shape without external influences is inherently stable. Materials of this type can be elastically deformable by forces with the result that after the forces are removed the materials assume their original shape. Alternatively, the materials can also be plastically deformable with the result that after the forces are removed they retain the shape which they have adopted as a result of the forces.

Insofar as is required, it is possible to connect the flexible material to the inherently stable material by way of a releasable connection, for example by way of a hook-loop fastener, trade mark name: Velcro tape) and/or a screw connection having pressure strips. Other embodiments are also possible. In a similar manner, it is possible to connect the flexible material to the transmit and/or receive facility. However, other embodiments are also possible in this case, for example pressing over an elastic band (O-ring or the like) or similar elements. The elastic band (if it is used) can be incorporated for example into the flexible material.

It is preferred that the transmit and/or receive facility has a depression that extends essentially parallel to the wall in the proximity of the transmit and/or receive facility. The depression can be designed for example as a circumferential groove. The depression can serve in particular to receive the elastic band (or the like).

In accordance with FIG. 1, a computed tomography unit 1 (inter alia) has a base body 1 and a part 4 that is able to rotate about an axis of rotation 3. The base body 2 is a fixed part. The rotatable part 4 is a part that is able to rotate relative to the fixed part about an axis of rotation 3.

Insofar as the terms "axial", "radial" and "tangential" are used in the text below, they always relate to the axis of rotation 3. "Axial" describes a direction parallel to the axis of rotation 3. "Radial" describes a direction orthogonal to the axis of rotation 3 toward the axis of rotation 3 or away from it. "Tangential" describes a direction that extends both orthogonal with respect to the axial direction and also orthogonal with respect to the radial direction. "Tangential" is therefore a direction that in a constant radial spacing from the axis of rotation 3 in the case of a constant axial position is oriented in a circular manner about the axis of rotation 3.

The computed tomography unit 1 as a whole is a device within the meaning of the present invention. In conjunction with the computed tomography unit 1, the present invention is further explained below. Therefore, in the text below the computed tomography unit 1 is always referred to as a device and the reference numeral 1 is also used. However, the present invention is not limited to an application in the case of a computed tomography unit 1. It can likewise also be used in the case of another device that has a first and a second part, wherein one of these two parts is a part that is able to rotate relative to the other part about an axis of rotation. Another example of a device of this type is a tank whose hull can be viewed as a fixed part and whose turret can be viewed as a rotatable part. Another example of a device of this type is a radar system in which the support structure of the rotating radar antenna can be regarded as a rotating part and the support structure is rotatably mounted in a base body of the radar system. Further examples are an electric machine having a rotor and stator, a wind turbine and a turbine. Other embodiments are also possible.

Within the scope of at least one embodiment of the present invention, in the text below the fixed base body 2 is regarded as a first part within the meaning of the present invention and the part 4 that is able to rotate about the axis of rotation 3 is regarded as the second part within the meaning of at least one embodiment of the present invention. Accordingly, in the text below the reference numerals 2 and 4 are also used for the first part and the second part. However, in principle, the reverse allocation would also be possible.

In many embodiments of the device 1 in accordance with the invention—for example in the case of a computed tomography unit 1—the extent to which the rotatable part 4 can rotate about the axis of rotation 3 is unlimited. It is thus not only possible to perform smaller rotational movements over a limited angle range but rather it is also possible to perform any number of complete rotations and also "crooked" rotations around for example 5.29 rotations. In some embodiments, it is however possible that only a limited amount of rotatability is available, for example over an angle of 60°, 180° or 300° or even a complete 360° (or slightly less).

Data is to be transmitted in a contactless manner from the fixed part 2 to the rotatable part 4 (and/or conversely). For this purpose, the device 1 in accordance with the illustration in FIGS. 2 to 4 has corresponding data transmission structures 5.

The data transmission structures 5 comprise initially (at least) one transmit and/or receive facility 6, referred to below in short as a transceiver. The transceiver 6 is arranged on the first part 2. In the event that the transceiver 6 is embodied as a transmitter, the transceiver 6 in fact transmits data but does not receive any data. In the event that that the transceiver 6 is embodied as a receiver, the transceiver 6 in fact receives data but does not transmit any data. In the event that the transceiver 6 is embodied both as a transmitter and also as a receiver, the transceiver 6 transmits data and receives other data. The data transmission structures 5 comprise furthermore a coupling facility 7. The coupling facility 7 is arranged on the second part 4. A further transceiver 8—so to say as a counterpart to the transceiver 8—is furthermore arranged on the second part 4. The further transceiver 8 can as required communicate in a contactless manner or contact-based manner with the coupling facility 7.

In the present case, it depends upon the geometric design and arrangement of the device 1. The arrangement of the further transceiver and the manner in which data is transmitted between the coupling facility 7 and the further transceiver 8 is of less importance for the geometric design of the device 1. The further transceiver 8 is therefore not mentioned further below. The further transceiver 8 is also not to be regarded as a component of the data transmission structures 5 within the meaning of at least one embodiment of the present invention.

Data can be transmitted between the transceiver 6 and the coupling facility 7 at an in principle arbitrary transmission frequency f. However, the embodiment in accordance with the invention renders it possible in particular for data to be transmitted according to the illustration in FIG. 4 at a transmission frequency f in the Gigahertz range, for example at a transmission frequency f that is between 3 GHz and 20 GHz, in part even up to 30 GHz.

Figure 3:
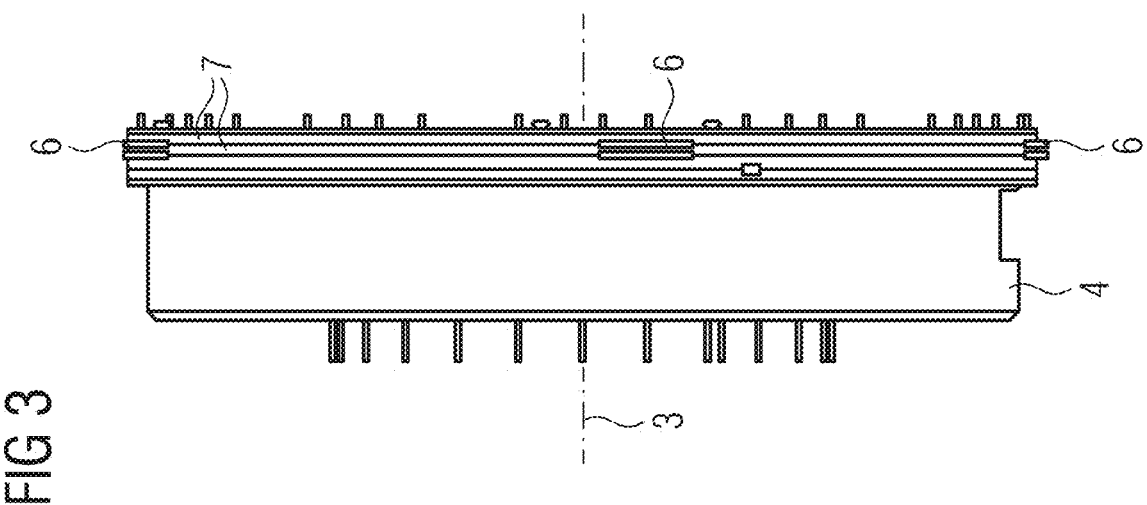
Figure 2:
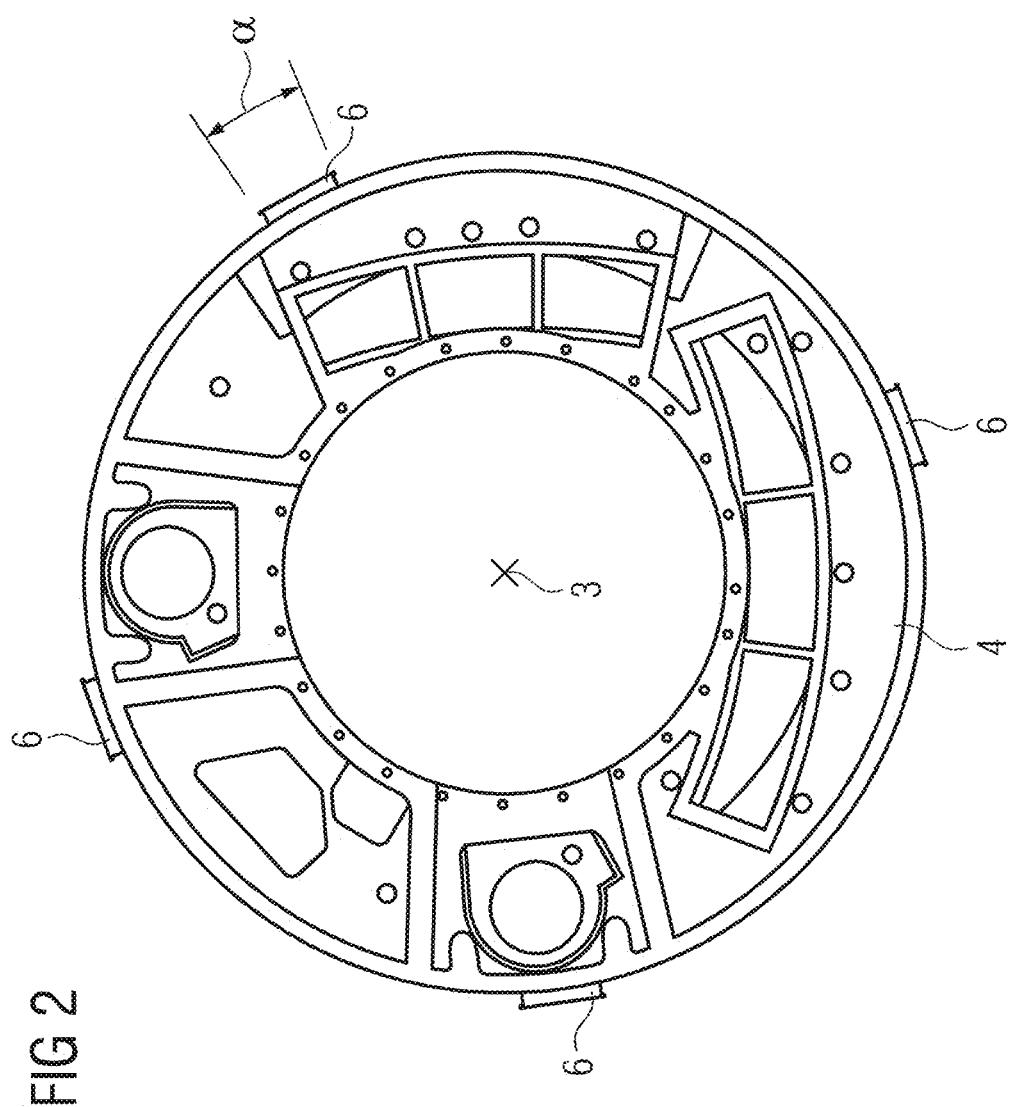
Figure 4:
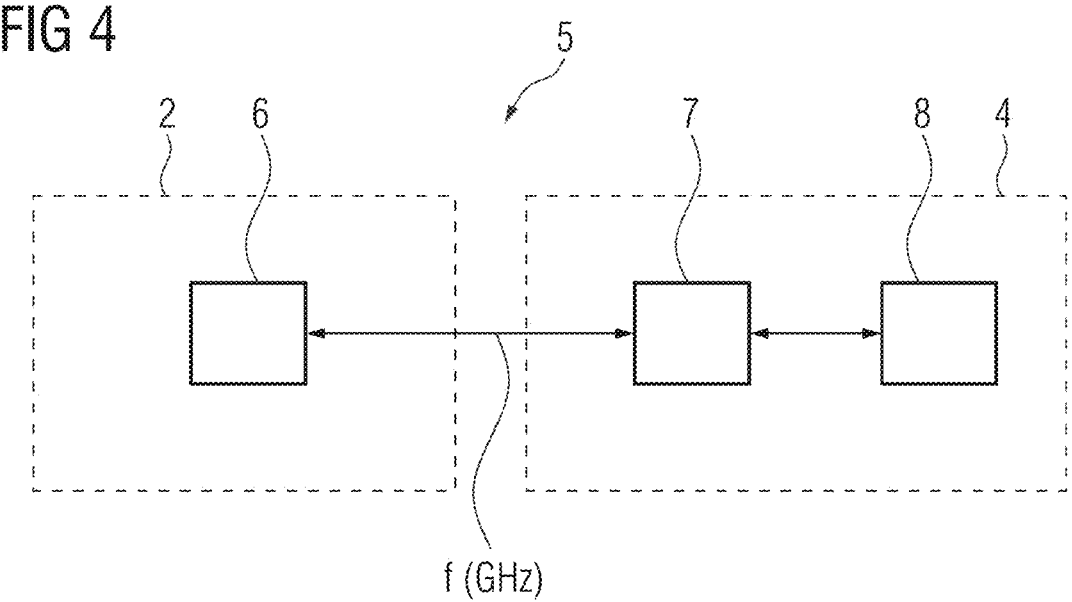
Figure 5:
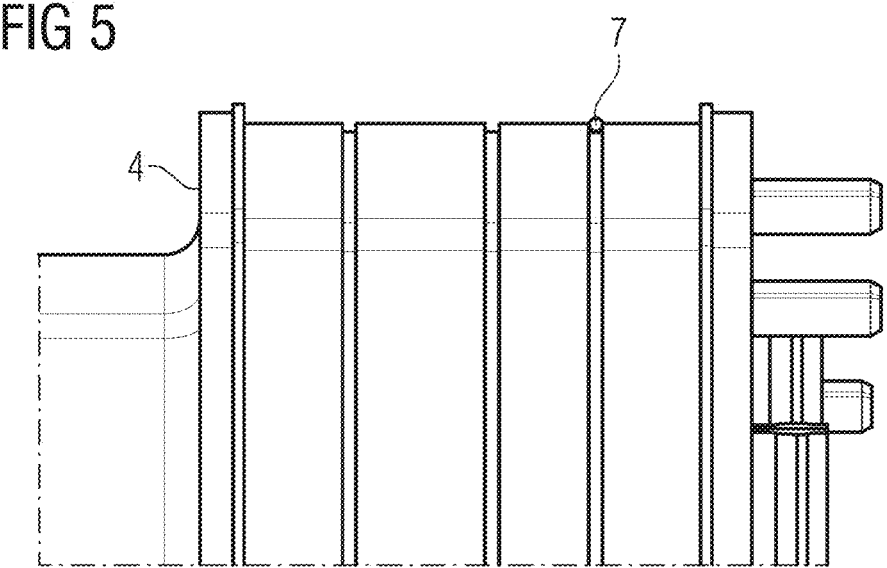

According to the illustration in FIGS. 2 and 3, the transceiver 6 extends in a tangential direction only over a small angle α. The angle α is mainly in the region of 15° or less, for example approx. 10°. The associated coupling facility 7 on the other hand extends in the tangential direction over a complete circle, in other words over the complete 360°. The coupling facility 7 can be designed for example in accordance with FIG. 5 as a coaxial cable that is embedded in a groove or channel of the second part 4 that is provided for this purpose. In this case, the shield and the outer conductor of the coaxial cable can be removed in the region that is facing the transceiver 6 when viewed in the axial-radial plane. As a consequence—depending upon the direction of the data transmission—it is possible to couple in or uncouple data from the transceiver 6 into the coupling facility 7 or conversely.

Furthermore, in particular in FIG. 2, two larger circular cut-outs and two larger elongated cut-outs are apparent. In the case of the specific embodiment of the second part 4, the two circular cut-outs serve as a drum of a computed tomography unit 1 to receive X-ray sources. The two elongated cut-outs serve to receive X-ray detectors. Although this fact is relevant within the scope of the specific embodiment as a computed tomography unit 1, it is however of less importance for the core idea of the present invention.

However, in accordance with the illustration in FIG. 3 (see in addition also FIG. 5), the transceiver 6 and the coupling facility 7 are located in the case of the same axial position spaced radially apart from one another. A connecting line from the transceiver 6 to the coupling facility 7 consequently has exclusively a radial component. It is likewise conversely also possible that although the transceiver 6 and the coupling facility 7 are in fact located in the case of the same radial position, they are spaced apart axially from one another. In this case, a connecting line from the transceiver 6 to the coupling facility 7 has exclusively an axial component. It would likewise also be possible in the case of a suitable arrangement and orientation of the transceiver 6 and the coupling facility 7 that a connecting line from the transceiver 6 to the coupling facility 7 has both an axial component and also a radial component. In this case, both the axial position and also the radial position of the transceiver 6 would differ from that of the coupling facility.

For the sake of good order, it is further mentioned that in FIG. 3 multiple coupling facilities 7 are illustrated, specifically three coupling facilities 7. Furthermore, multiple transceivers 6 are also illustrated for two of the coupling facilities 7.

Figure 6:
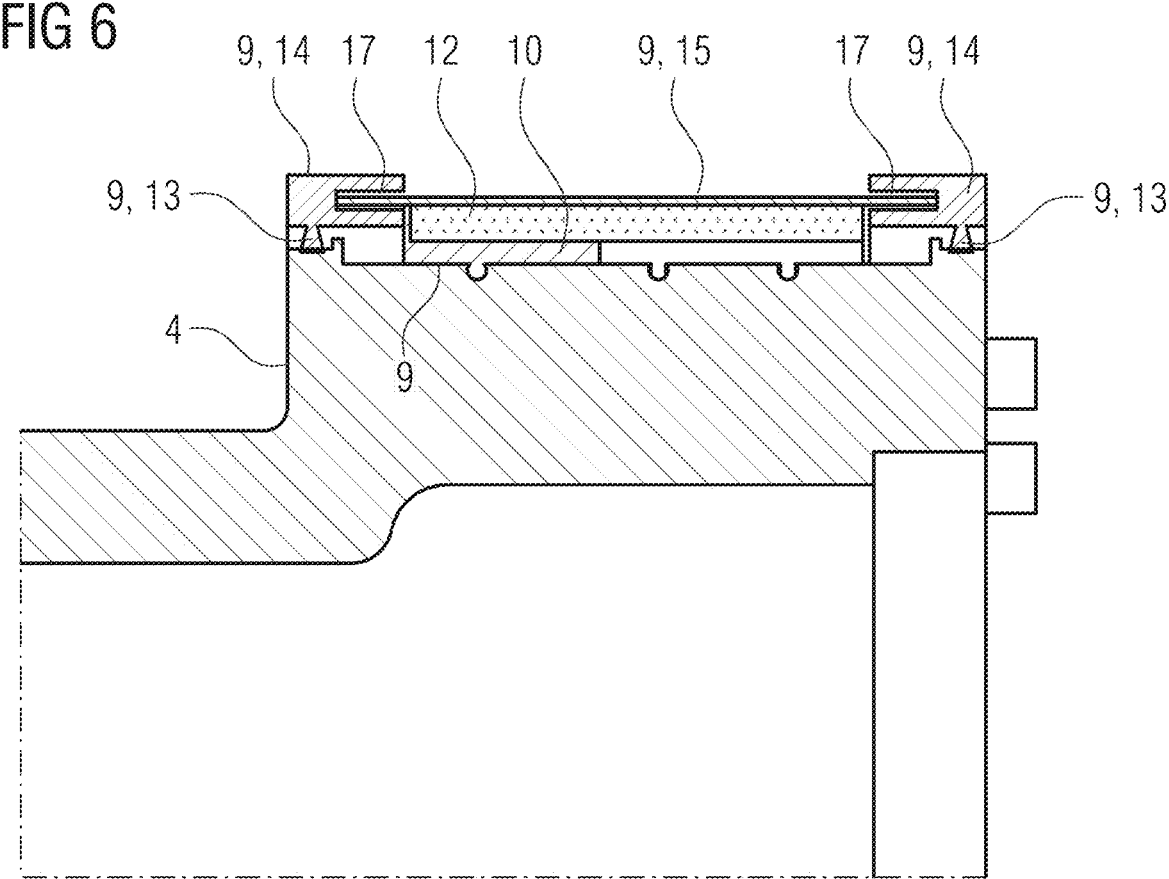
Figure 7:
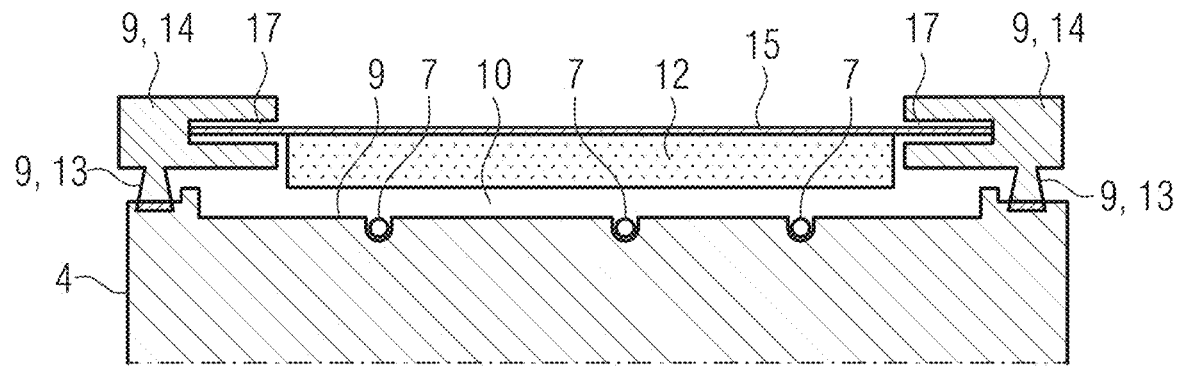
Figure 8:
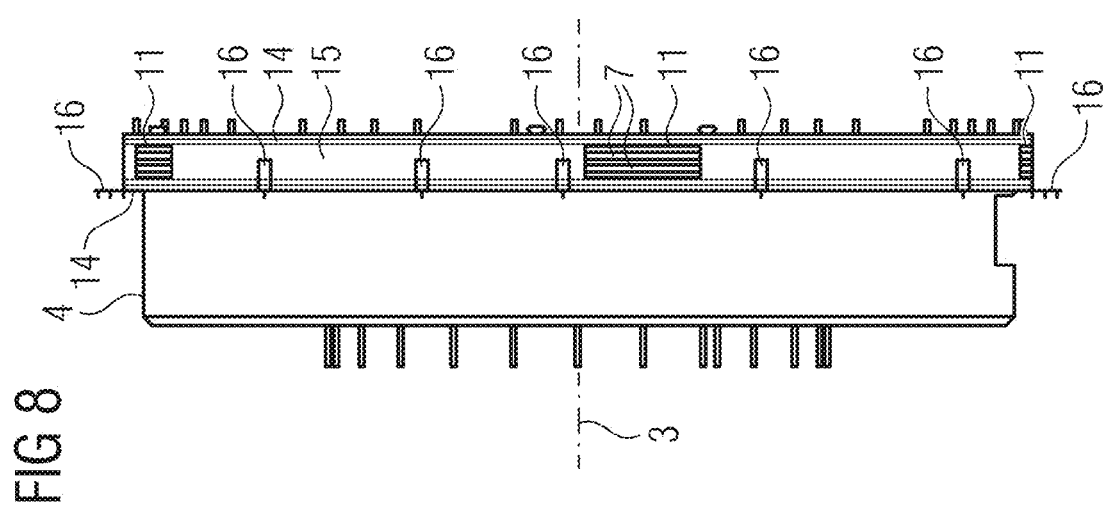

According to the illustration in FIGS. 6, 7 and 8, the first and the second part 2, 4 have walls 9 so as to shield electromagnetic waves that occur within the scope of data transmissions between the transceiver 6 and the coupling facility 7. The walls 9 delimit a tunnel interior space 10. The tunnel interior space 10 extends in the tangential direction over a complete circle. It therefore extends completely about the axis of rotation 3. Viewed in the axial-radial plane, the walls 9 completely encompass the tunnel interior space 10. Thus, viewed in the tangential direction, the walls 9 also extend over a complete circle, in other words completely about the axis of rotation 3. This is particularly clearly apparent in FIG. 8. Reference is made in this connection to the fact that the cut-outs 11 that are apparent in FIG. 8 will be further explained later. The data transmission structures 5—in other words within the scope of at least one embodiment of the present invention the transceiver 6 and the coupling facility 7 but not the further transceiver 8—are arranged in the tunnel interior space 10 or protrude into the tunnel interior space 10. The cut-outs 11 are larger than the transceiver 6. This renders it possible to adjust the transceiver 6 as required relative to its respective coupling facility 7.

The walls 9 are embodied as electrically conductive structures. For example, they can be formed from metal or they can be metal coated. This applies—but not exclusively, probably however inter alia—also for the second part 4 at least in the region that delimits the tunnel interior space 10. Due to the design as electrically conductive structures, the walls 9 reflect electromagnetic alternating fields at least in the range of the transmission frequency f.

Furthermore, an absorber structure 12 is arranged at least on a part of the walls 9 toward the tunnel interior 10. The absorber structure 12 absorbs electromagnetic alternating fields at least in the region of the transmission frequency f. The absorber structure 12 can be designed as a foam. This is indicated in FIG. 7 by a corresponding dotting of the absorber structure 12. It is preferred that the absorber structure 12 likewise extends in a tangential direction completely about the axis of rotation 3.

Viewed in the axial-radial plane, the walls 9 encompass the tunnel interior space 10 without any gaps. For this purpose, the walls 9 are designed in the transition regions from the first to the second part 2, 4 as elastic structures 13 having two ends. One end of the elastic structures 13 is fastened to a respective retaining structure 14. The retaining structures 14 are in turn arranged on the first or on the second part 2, 4. The other end of the elastic structures 13 is pressed against the respective other part 4, 2. If, in other words, the retaining structures 14 are arranged on the first part 2, the elastic structures 13 are pressed against the second part 4. This embodiment represents the general case and is preferred. If (as an exception) the retaining structures 14 are arranged on the second part 4, the elastic structures 13 are pressed against the first part 2. The elastic structures 13 can be designed in particular according to the illustration in FIG. 9 as brush hairs. Where appropriate, the brush hairs are close to one another and are preferably arranged in multiple rows. Purely as an example, three rows of brush hairs are illustrated in FIG. 9.

The retaining structures 14 are spaced apart from one another in the axial direction according to the illustration in FIGS. 6 to 8. However, as an alternative or in addition, in the case of a corresponding arrangement of the data transmission structures 5, they could also be spaced apart from one another in the radial direction. So as to bridge the gap between the holding structures 14, a carrier plate 15 is inserted into the holding structures 14. Where necessary, the carrier plate 15 can be fixed in addition by fixing elements 16 (cf. FIG. 8). According to the illustration in FIG. 7, the absorber structure 12 is arranged on the carrier plate 15. This embodiment is preferred but not absolutely necessary.

Figure 9:
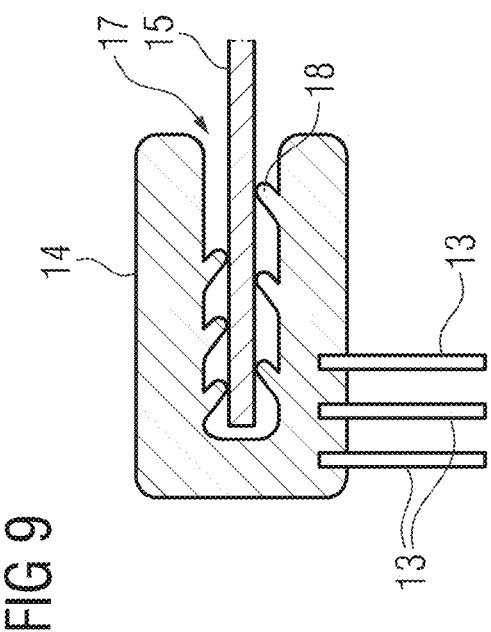

It is preferred that the retaining structures 14 have-cf. in particular FIG. 9—corresponding receiving facilities 17 for receiving the carrier plate 15. In this case, it is preferred that lamellae 18 are arranged in the receiving facilities 17. The receiving facilities 17 are electromagnetically sealed via the lamellae 18 with respect to the carrier plate 15 at least in the range of the transmission frequency f. Furthermore, the carrier plate 15 is mechanically fixed in the receiving facilities 17 by the lamellae 18.

The elastic structures 13, the retaining structures 14 and the carrier plate 15 are, as already mentioned, components of the walls 9. They are therefore designed as electrically conductive, for example coated with metal. The same applies for the second part 4, at least insofar as it delimits the tunnel interior space 10.

Figure 10:
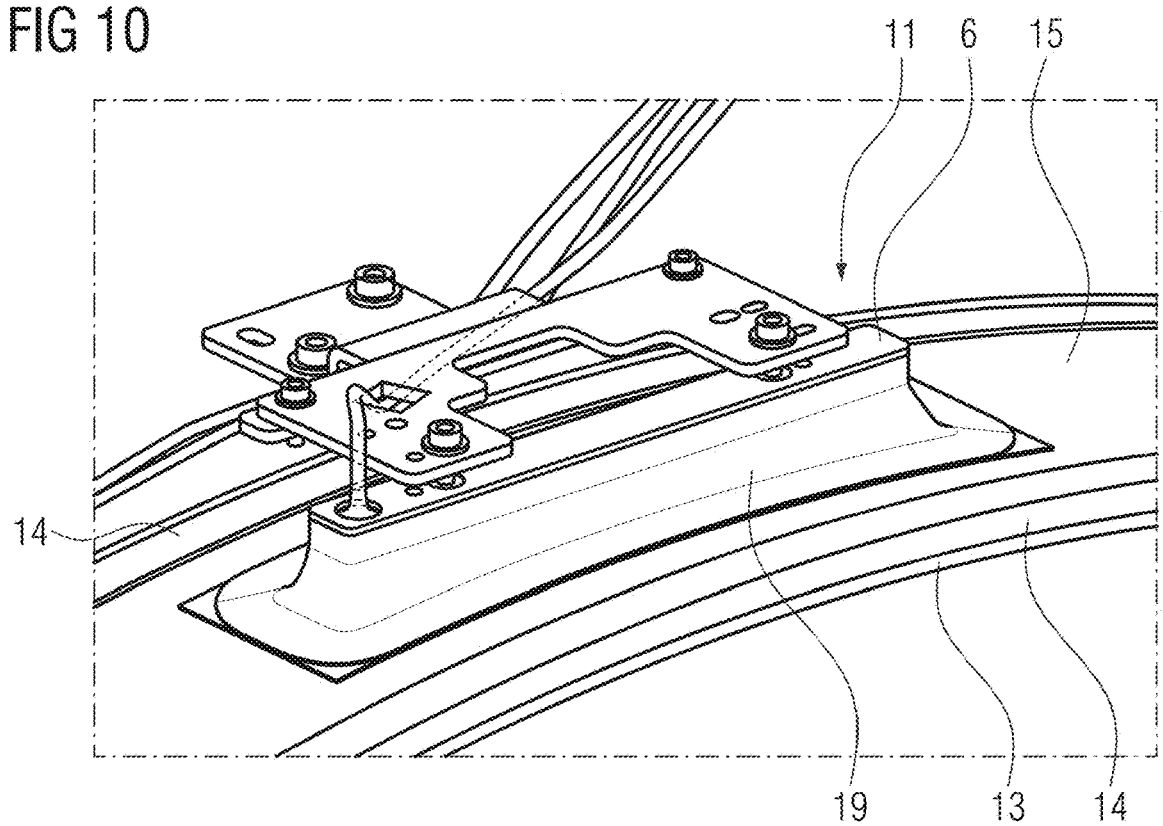

As already casually mentioned, the walls 9 have cut-outs 11. The cut-outs 11 serve so that the transceiver 6 (or a corresponding number of transceivers 6) can protrude into the tunnel interior space 10. FIG. 10 shows an example of such a cut-out 11 including the associated transceiver 6 and the manner in which a complete electromagnetic sealing or shielding of the tunnel interior space 10 is achieved in the region of the cut-out 11 and the transceiver 6.

In accordance with FIG. 10, the wall 9, insofar as it is arranged on the first part 2, is formed from a flexible material 19 at least in the region in which the wall 9 adjoins the transceiver 6. The flexible material 19 can be for example a conductive material or a conductive fabric. It is particularly preferred if the flexible material 19 does not have any inherent stability. As a consequence, the flexible material 19 does not exert any forces on the transceiver 6. A previous adjustment of the transceiver 6 relative to the coupling facility 7 is therefore not affected. However, outside the region of the wall 9 that adjoins the transceiver 6, the wall 9 that is arranged on the first part 2 can easily be formed from an inherently stable material. For example, the flexible material 19 can be connected at its end that is remote from the transceiver 6 to the carrier plate 15.

The flexible material 19 can be connected to the inherently stable material (for example the carrier plate 15) in a manner as required. The connection is preferably releasable. For example, the connection can comprise a hook-and-loop fastener and/or a screw connection. In the case of a screw connection, (a part of screw connections of this type is shown in FIG. 11), the screw connection presses the flexible material against the inherently stable material preferably by way of relatively large pressure strips (not illustrated).

The flexible material 19 can be connected to the transceiver 6 in the same manner as the connection of the flexible material 19 to the inherently stable material. Alternatively, the connection can be made in a different manner. It is preferred that pressure is provided by way of an elastic, closed element 20 (cf. FIG. 12), for example an elastic band, an O-ring or a similar element. In particular, it is possible that the elastic, closed element 20 is incorporated into the flexible material 19 according to the illustration in FIG. 12. According to the illustration in FIG. 11, the transceiver 6 has—in particular in its region that is furthermost away from the tunnel interior space 10 —a depression 21 which renders it possible for example to ensure that it is fixed to the transceiver 6. The depression 21 extends in this case essentially parallel to the wall 9 in the proximity of the transceiver 6. It serves to receive the elastic, closed element 20. It can be designed for example as a circumferential groove or as a circumferential channel.

Figure 11:
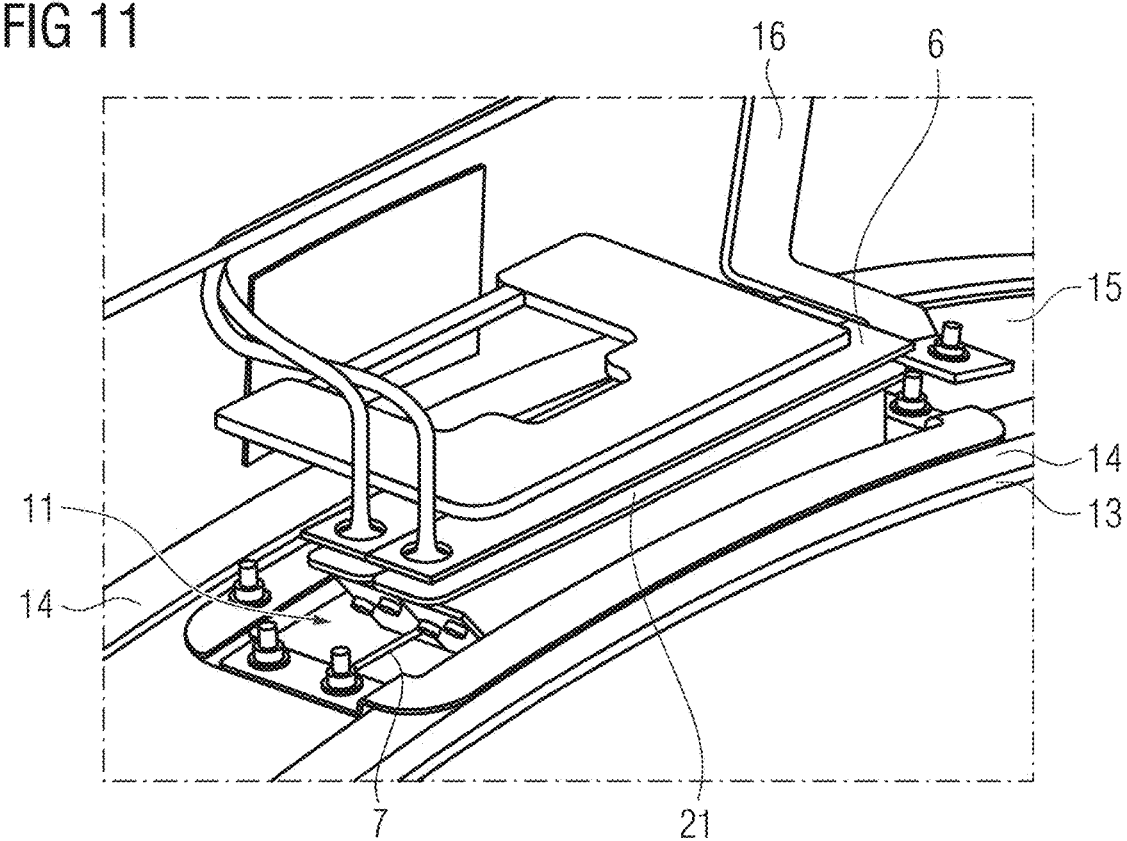
Figure 12:
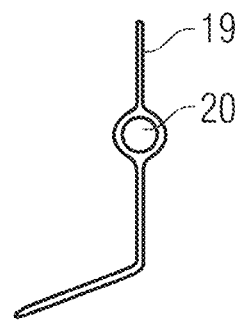

Furthermore, FIGS. 10 and 11 also illustrate the mechanical fixing and the electrical connection of the transceiver 6. However, this is of less importance within embodiments of the scope of the present invention.

As an alternative to a combination of a flexible material 19 and an inherently stable material (for example of the carrier plate 15), it is also possible to produce large parts of the walls 9 from the flexible material 19. This embodiment has the advantage that it is also possible to shield in a simple manner complex structures, such as for example interference regions due to other components.

To summarize, at least one embodiment of the present invention thus relates to the following facts:

A device 1 has a first and a second part 2, 4, of which one part 4 is able to rotate relative to the other part 2 about an axis of rotation 3. The device 1 has data transmission structures 5 for the contactless transmission of data, the data transmission structures comprising a transmit and/or receive facility 6 that is arranged on the first part 2 and a coupling facility 7 that is arranged on the second part 4. Viewed in the circumferential direction about the axis of rotation 3, the transmit and/or receive facility 6 extends over a small angle α and the coupling facility 7 extends over a complete circle. Data is transmitted between the transmit and/or receive facility 6 and the coupling facility 7 at a transmission frequency f. The two parts 2, 4 have walls 9 that jointly completely encompass a tunnel interior space 10 that completely extends around the axis of rotation 3. The data transmission structures 5 are arranged in the tunnel interior space 10 or protrude therein. The walls 9 are electrically conductive structures that reflect electromagnetic alternating fields in the range of the transmission frequency f. An absorber structure 12 is arranged at least on a part of the walls 9 toward the tunnel interior space 10 and the absorber structure absorbs electromagnetic alternating fields in the range of the transmission frequency f.

The present invention has many advantages. In particular, it is possible to easily form a completely closed tunnel around the data transmission structures 5. This renders possible a shielding in the GHz range.

Although the invention has been further illustrated and described in detail with the aid of the preferred example embodiment, the invention is not limited by the disclosed examples and other variations can be derived therefrom by the person skilled in the art without abandoning the protective scope of the invention.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device, comprising:
   a first part and second part, one of the first part and the second part being a part rotatable relative to another one of the first part and the second part, about an axis of rotation;
   data transmission structures for contactless transmission of data, the data transmission structures including at least one of a transmit and receive facility, arranged on the first part, and a coupling facility arranged on the second part,
   wherein, when viewed in a circumferential direction about the axis of rotation, the at least one of transmit and receive facility extends over a small angle and the coupling facility extends over a complete circle,
   wherein data is transmitted between the at least one of transmit and receive facility and the coupling facility at a transmission frequency,
   the first part and the second part including walls jointly completely encompassing a tunnel interior space extending completely around the axis of rotation,
   the data transmission structures being arranged in the tunnel interior space or protruding into the tunnel interior space,
   the walls being formed as electrically conductive structures configured to reflect electromagnetic alternating fields in a range of the transmission frequency; and
   an absorber structure, arranged at least on a part of the walls toward the tunnel interior space, to absorb electromagnetic alternating fields in the range of the transmission frequency.

2. The device of claim 1, wherein the walls are designed, in transition regions from the first part to the second part, as elastic structures having two ends, one end being fastened to a retaining structure respectively arranged on the first part or the second part and another end being pressed against the second part or the first part.

3. The device of claim 2, wherein the elastic structures are designed as brush hairs.

4. The device of claim 3, wherein retaining structures are spaced apart from one another with regard to the axis of rotation in at least one of an axial and a radial direction and wherein a carrier plate bridging the retaining structures is inserted into the retaining structures.

5. The device of claim 4, wherein the retaining structures include receiving facilities for receiving the carrier plate and wherein, arranged in the receiving facilities, are lamellae via which the receiving facilities are electromagnetically sealed with respect to the carrier plate in the range of the transmission frequency and wherein the carrier plate is mechanically fixed in the receiving facilities.

6. The device of claim 2, wherein retaining structures are spaced apart from one another with regard to the axis of rotation in at least one of an axial and a radial direction and wherein a carrier plate bridging the retaining structures is inserted into the retaining structures.

7. The device of claim 6, wherein the retaining structures include receiving facilities for receiving the carrier plate and wherein, arranged in the receiving facilities, are lamellae via which the receiving facilities are electromagnetically sealed with respect to the carrier plate in the range of the transmission frequency and wherein the carrier plate is mechanically fixed in the receiving facilities.

8. The device of claim 7, wherein the absorber structure is arranged on the carrier plate.

9. The device of claim 6, wherein the absorber structure is arranged on the carrier plate.

10. The device of claim 2, wherein the retaining structures are arranged on the first part.

11. The device of claim 2, wherein the absorber structure is designed as a foam.

12. The device of claim 2, wherein the wall arranged on the first part is formed from a flexible material at least in a region adjoining the at least one of transmit and receive facility.

13. The device of claim 12, wherein the flexible material is a conductive material or a conductive fabric.

14. The device of claim 1, wherein the absorber structure is designed as a foam.

15. The device of claim 1, wherein the wall arranged on the first part is formed from a flexible material at least in a region adjoining the at least one of transmit and receive facility.

16. The device of claim 15, wherein the flexible material is a conductive material or a conductive fabric.

17. The device of claim 16, wherein the wall arranged on the first part is formed from an inherently stable material outside the region adjoining the at least one of transmit and receive facility.

18. The device of claim 15, wherein the wall arranged on the first part is formed from an inherently stable material outside the region adjoining the at least one of transmit and receive facility.

19. The device of claim 1, wherein the at least one of transmit and receive facility includes a depression extending essentially parallel to the wall in proximity of the at least one of transmit and receive facility.

* * * * *